United States Patent
Deliwala

(10) Patent No.: US 12,228,502 B2
(45) Date of Patent: Feb. 18, 2025

(54) GAS DETECTION USING DIFFERENTIAL PATH LENGTH MEASUREMENT

(71) Applicant: Analog Devices, Inc., Wilmington, MA (US)

(72) Inventor: Shrenik Deliwala, Andover, MA (US)

(73) Assignee: ANALOG DEVICES, INC., Wilmington, MA (US)

( * ) Notice: Subject to any disclaimer, the term of this patent is extended or adjusted under 35 U.S.C. 154(b) by 236 days.

(21) Appl. No.: 18/066,766

(22) Filed: Dec. 15, 2022

(65) Prior Publication Data

US 2023/0120444 A1   Apr. 20, 2023

Related U.S. Application Data

(62) Division of application No. 16/872,758, filed on May 12, 2020, now Pat. No. 11,747,272.

(Continued)

(51) Int. Cl.
  *G01N 21/3504* (2014.01)
  *G01N 33/00* (2006.01)

(52) U.S. Cl.
  CPC ....... *G01N 21/3504* (2013.01); *G01N 33/004* (2013.01); *G01N 2201/062* (2013.01);
  (Continued)

(58) Field of Classification Search
  CPC ............. G01N 21/3504; G01N 33/004; G01N 2201/062; G01N 2201/0668;
  (Continued)

(56) References Cited

U.S. PATENT DOCUMENTS

| | | |
|---|---|---|
| 4,148,022 A | 4/1979 | Hetznecker |
| 4,181,439 A | 1/1980 | Tresch et al. |

(Continued)

FOREIGN PATENT DOCUMENTS

| | | |
|---|---|---|
| CA | 2386899 A1 | 4/2001 |
| CN | 104246617 B | 9/2018 |

(Continued)

OTHER PUBLICATIONS

International Search Report and Written Opinion in PCT/US2018/035203, mailed Aug. 29, 2018, 11 pages.

(Continued)

*Primary Examiner* — Mohamed K Amara
(74) *Attorney, Agent, or Firm* — ArentFox Schiff LLP

(57) ABSTRACT

Device for improving an optical detecting smoke apparatus and implementing thereof. Apparatus and methods for detecting the presence of smoke in a small, long-lasting smoke detector are (disclosed. Specifically, the present disclosure shows how to build one or more optimized blocking members in a smoke detector to augment signal to noise ratio. This is performed while keeping the reflections from the housing structure to a very low value while satisfying all the other peripheral needs of fast response to smoke and preventing ambient light. This allows very small measurements of light scattering of the smoke particles to be reliable in a device resistant to the negative effects of dust. In particular, geometrical optical elements, e.g., cap and optical defection elements, are disclosed.

20 Claims, 9 Drawing Sheets

Related U.S. Application Data

(60) Provisional application No. 62/859,276, filed on Jun. 10, 2019.

(52) U.S. Cl.
    CPC ............... *G01N 2201/0668* (2013.01); *G01N 2201/0686* (2013.01)

(58) Field of Classification Search
    CPC ....... G01N 2201/0686; G01N 21/3151; G01N 21/0303; G01N 33/497; G01N 2021/3133; G01N 2021/3174; G01N 2021/3181; G01N 33/0022; G01N 2201/0221; G01N 2201/0636; G01N 2201/0662; G01J 3/0208; G01J 3/42; G08B 17/107; Y02A 50/20
    See application file for complete search history.

(56) References Cited

U.S. PATENT DOCUMENTS

| | | | |
|---|---|---|---|
| RE32,105 E | 4/1986 | Enemark | |
| 4,618,771 A | 10/1986 | Farren | |
| 4,830,496 A | 5/1989 | Young | |
| 5,129,401 A | 7/1992 | Corenman et al. | |
| 5,382,341 A | 1/1995 | Aroutiounian et al. | |
| 5,420,440 A | 5/1995 | Ketler et al. | |
| 5,444,249 A | 8/1995 | Wong | |
| 5,568,129 A | 10/1996 | Sisselman et al. | |
| 5,689,114 A | 11/1997 | Miyazaki et al. | |
| 5,781,291 A | 7/1998 | So et al. | |
| 5,957,858 A | 9/1999 | Micheels et al. | |
| 5,966,077 A | 10/1999 | Wong | |
| 5,973,326 A | 10/1999 | Parry et al. | |
| 6,122,042 A * | 9/2000 | Wunderman | A61B 1/0607 356/73 |
| 6,194,735 B1 | 2/2001 | Martin | |
| 6,599,253 B1 | 7/2003 | Baum et al. | |
| 6,721,057 B1 * | 4/2004 | Reininger | G01J 3/4531 356/450 |
| 8,003,945 B1 | 8/2011 | Wong | |
| 8,232,885 B2 | 7/2012 | Hoshino et al. | |
| 10,436,713 B2 * | 10/2019 | Battrell | B01L 7/52 |
| 11,073,467 B2 | 7/2021 | Santangelo et al. | |
| 11,079,321 B2 | 8/2021 | Castagna et al. | |
| 11,821,836 B2 * | 11/2023 | Deliwala | G01N 33/0009 |
| 2003/0011769 A1 | 1/2003 | Rakuljic et al. | |
| 2004/0021078 A1 * | 2/2004 | Hagler | G01J 3/06 250/339.13 |
| 2004/0072535 A1 | 4/2004 | Schneider et al. | |
| 2005/0077489 A1 | 4/2005 | Knapp et al. | |
| 2007/0013883 A1 | 1/2007 | Park | |
| 2007/0145275 A1 | 6/2007 | Wong | |
| 2007/0221848 A1 | 9/2007 | Johnson et al. | |
| 2008/0316489 A1 | 12/2008 | Ludwig | |
| 2009/0213380 A1 | 8/2009 | Appel et al. | |
| 2009/0235720 A1 | 9/2009 | Smith | |
| 2009/0257064 A1 | 10/2009 | Tkachuk | |
| 2009/0268204 A1 * | 10/2009 | Tkachuk | G01N 21/3504 356/437 |
| 2011/0042570 A1 | 2/2011 | Wong | |
| 2011/0178420 A1 | 7/2011 | Ridder et al. | |
| 2012/0135405 A1 | 5/2012 | Toumbas et al. | |
| 2012/0140231 A1 | 6/2012 | Knox et al. | |
| 2012/0267532 A1 | 10/2012 | Udrea et al. | |
| 2013/0066173 A1 | 3/2013 | Addison et al. | |
| 2013/0075615 A1 | 3/2013 | Starta et al. | |
| 2013/0286393 A1 | 10/2013 | Erdtmann | |
| 2014/0070101 A1 | 3/2014 | Matsushima et al. | |
| 2015/0129767 A1 | 5/2015 | Kouznetsov et al. | |
| 2015/0219491 A1 | 8/2015 | Lee et al. | |
| 2016/0005921 A1 | 1/2016 | Suchalkin et al. | |
| 2016/0042638 A1 | 2/2016 | Sangha et al. | |
| 2016/0231239 A1 | 8/2016 | Kotidis et al. | |
| 2017/0191930 A1 | 7/2017 | Warren et al. | |
| 2017/0241904 A1 | 8/2017 | Barritault et al. | |
| 2018/0172517 A1 * | 6/2018 | Grueger | G01J 3/0256 |
| 2018/0348121 A1 | 12/2018 | Deliwala | |
| 2019/0094134 A1 | 3/2019 | Solovyov et al. | |
| 2019/0219497 A1 * | 7/2019 | Peter | G02B 5/32 |
| 2020/0209158 A1 | 7/2020 | Nikolaenko et al. | |
| 2021/0072082 A1 | 3/2021 | Valouch et al. | |
| 2021/0132019 A1 | 5/2021 | Heffels et al. | |

FOREIGN PATENT DOCUMENTS

| | | | | |
|---|---|---|---|---|
| DE | 102017213196 A1 | 1/2019 | | |
| EP | 896216 A2 | 2/1999 | | |
| JP | H09229585 A | 9/1997 | | |
| JP | 2024109619 A * | 8/2024 | | G01J 3/0208 |
| WO | 9914576 A2 | 3/1999 | | |
| WO | 2007080398 A1 | 7/2007 | | |
| WO | 2009150325 A1 | 12/2009 | | |

OTHER PUBLICATIONS

International Search Report and Written Opinion in PCT/US2021/041378, mailed Jan. 28, 2022, 18 pages.

Invitation to Pay Additional Fees for PCT/US2021/041378, mailed Oct. 19, 2021, 10 pages.

Paul et al., "Investigation of gas sensor based on differential optical absorption spectroscopy using photonic crystal fiber," Alexandria Engineering Journal, Dec. 2020, vol. 59, No. 6, pp. 5045-5052.

Yang et al., "Simultaneous measurement of gas absorption and path length by employing the first harmonic phase angle method in wavelength modulation spectroscopy," Optics Express, Feb. 2020, vol. 28, No. 3, pp. 3289-3297.

\* cited by examiner

GAS DETECTION USING DIFFERENTIAL PATH LENGTH MEASUREMENT

CROSS-REFERENCE TO RELATED APPLICATIONS

This application is a divisional (and claims benefit of priority under 35 U.S.C. § 121 of U.S. application Ser. No. 16/872,758 filed May 12, 2020, entitled GAS DETECTION USING DIFFERENTIAL PATH LENGTH MEASUREMENT" and related to and claims the benefit of priority under 35 U.S.C. § 119 (e) to U.S. Provisional Patent Application No. 62/859,276 entitled, "GAS DETECTION USING DIFFERENTIAL PATH LENGTH MEASUREMENT" filed on Jun. 10, 2019 and related to U.S. patent application Ser. No. 15/993,188 entitled, "COMPACT OPTICAL GAS DETECTION SYSTEM AND APPARATUS" filed on May 30, 2018, all of which are hereby incorporated by reference in their entirety.

FIELD OF THE DISCLOSURE

The present disclosure relates to portable gas detection. More specifically, this disclosure describes apparatuses and systems for optical gas detection using differential path lengths.

BACKGROUND

A nondispersive infrared sensor (or NDIR sensor) is a simple spectroscopic sensor often used as a gas detector. It is nondispersive in the sense of optical dispersion since the infrared energy is allowed to pass through the atmospheric sampling chamber without deformation.

It is a so non-dispersive in the fact that no dispersive element (e.g., a prism or diffraction grating as is often present in other spectrometers) is used to separate out (like a monochromator) the broadband light into a narrow spectrum suitable for gas sensing. The majority of NDIR sensors use a broadband lamp source and an optical filter to select a narrow band spectral region that overlaps with the absorption region of the gas of interest. In this context narrow may be 50-300 nm bandwidth. Modern NDIR sensors may use Microelectromechanical systems (MEMs) or mid IR LED sources, with or without an optical filter.

The main components of an NDIR sensor are an infrared source (lamp), a sample chamber or light tube, a light filter and an infrared detector. The IR light is directed through the sample chamber towards the detector. In parallel there is another chamber with an enclosed reference gas, typically nitrogen. The gas in the sample chamber causes absorption of specific wavelengths according to the Beer-Lambert law, and the attenuation of these wavelengths is measured by the detector to determine the gas concentration. The detector has an optical filter in front of it that eliminates a light except the wavelength that the selected gas molecules can absorb.

ideally other gas molecules do not absorb light at this wavelength, and do not affect the amount of light reaching the detector however some cross-sensitivity is inevitable. For instance, many measurements in the IR area are cross sensitive to H2O so gases like CO2, SO2 and NO2 often initiate cross sensitivity in low concentrations.

A common application is to use a NDIR (non-dispersive infrared absorbance) sensor to monitor CO2. Most molecules can absorb infrared light, causing them to bend, stretch or twist. The amount of IR light absorbed is proportional to the concentration. The energy of the photons is not enough to cause ionization, and thus the detection principle is very different from that of a photoionization detector (PID). Ultimately, the energy is converted to kinetic energy, causing the molecules to speed up and thus heat the gas. A familiar IR light source is an incandescent household bulb. Each molecule absorbs infrared light at wavelengths representative of the types of bonds present.

Many techniques have Peen proposed which typically consist of a broadband light source. Unfortunately, they require relatively long optical paths which reduce light collection efficiencies. The inventor of the present disclosure has identified these shortcomings and recognized a need for a more elegant, robust, compact optical gas detection measurement system with high collection efficiency. That is, the inventor has come up with a compact, low-power, optical gas detection apparatus which can be mass produced via packaging without yielding accuracy.

Additionally, the current state of the art uses color wheels or filters disposed at the photodetectors. Specifically, one color (at wavelength, $\lambda_1$) is measured for an absorption for a particular gas. The reference measure is typically taken at another color (at wavelength, $\lambda_2$) via color wheel or second sensor with a filter centered at, $\lambda_2$. Gas concentration per unit volume is based upon absorption spectroscopy. However, these techniques fail to account for the variation of several parameters, in particular, thermal drift, filter bandwidth and sensitivity, variance of the source as a function of wavelength, etc.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

System and apparatus for robust, portable gas detection. Specifically, this disclosure describes apparatuses and systems for optical gas detection in a compact package. There is a need for a very compact, low-power, gas detection system for gases such as CO2, NOx, water vapor, methane, etc. This disclosure provides an ultra-compact and highly efficient optical measurement system based on principals of optical absorption spectroscopy.

It not only recuses the size of the instrument as well its power consumption by more than an order of magnitude making it possible to deploy it widely, but increases accuracy. This is accomplished by measuring two optical path lengths subject to the same conditions and thereby concluding a result, ceteris paribus. There has been an identified need for large number of distributed gas sensors to improve human health, environment, and save energy usage.

According to one aspect of the present disclosure, gas absorption measurement device (or working fluid absorption device) comprises a light source forming a common light path, one or more filters filtering the common light path, a collimator disposed in the common light path, a beam splitter to split the common light path and two or more detectors, each of which to collect the split light path.

According to another aspect of the present disclosure, gas absorption measurement device (or working fluid absorption device) is configure to dispose the two or detectors at two (or more accordingly) different distances from the light source with each detector measuring light transmission after two different gas absorption path lengths.

According to another aspect of the present disclosure, gas absorption measurement device (or working fluid absorption device) further comprises collector optic before the detectors.

According to another aspect of the present disclosure, gas absorption measurement device (or working fluid absorption device), the beam splitter can be a polarizing beam splitter (PBS), a half-wave plate, a half-silvered mirror, a Fresnel prism, or any other suitable optic.

According to another aspect of the present disclosure, gas absorption measurement device (or working fluid absorption device) further comprises one or more waveguides.

According to another aspect of the present disclosure, the waveguides provide for openings for the diffusion of gas molecules.

According to another aspect of the present disclosure, the optical filter can include an absorptive filter and/or interference or dichroic filter.

According to another aspect of the present disclosure, the gas absorption measurement device (or working fluid absorption device) further comprises a fiber-Bragg grating (FBG).

According to another aspect of the present disclosure, the light source can include a light emitting device (LED) or other suitable device.

According to another aspect of the present disclosure, the collection optics can include a convex or concave lens.

According to another aspect of the present disclosure, the detectors are photosensitive elements and can be one or more of the following: photodetectors, photodiodes (PDs), avalanche photodiodes (APDs), single-photon avalanche photodiode (SPADs), photomultipliers (PMTs).

According to another aspect of the present disclosure, the differences in the path length is employed after filtering of the light source for a specific gas absorption.

According to another aspect of the gas absorption measurement device (or working fluid absorption device), a ratio of the two detector signals is used to measure the concentration of the working fluid.

According to another aspect of the gas absorption measurement device (or working fluid absorption device), the ratio of the two detectors is saved during calibration step with known condition and subsequently used for future calculations.

According to another aspect of the gas absorption measurement device (or working fluid absorption device), concentration of a predetermined gas is calculated.

According to another aspect of the present disclosure, the predetermined gas may be CO2, water vapor, methane CH4, NO, as well as vapors of various alcohols.

According to another aspect of the present disclosure, the predetermined gas may be any of the gases used in anesthesia.

According to another aspect of the present disclosure, the predetermined gas may be vapors of diesel, kerosene, or gasoline.

According to another aspect of the present disclosure, multiple gases may be simultaneously detected by using multiple detectors with optical filters chosen for each of the gases and using a broadband light source.

According to another aspect of the present disclosure, the predetermined gases may be CO2 and alcohol vapor which are simultaneously detected for breadth analysis.

According to another aspect of the present disclosure, the predetermined gases may be water and alcohol vapor which are simultaneously detected for breadth analysis.

According to another aspect of the disclosure, the gas absorption measurement device (or working fluid absorption device) is disposed on a substrate.

According to another aspect of the present disclosure, the gas absorption measurement device (or working fluid absorption device) further comprises an optical cap to which is affixed to the substrate.

According to another aspect of the present disclosure, the inner shape of the cap forms a mirror in which the mirror shape is derived from the two elliptical mirror surfaces inclined substantially at 45 degrees to provide high collection of the light source to the detector.

According to another aspect of the present disclosure, the cap provides for openings for the diffusion of gas molecules.

According to another aspect of the present disclosure, the substrate and the cap provide a method of alignment to each other.

According to another aspect of the present disclosure, the opto-electronic package for measurement of absorption of light further comprises a substrate with at least two detectors disposed thereon.

According to another aspect of the present disclosure, wherein the first detector acts as a reference detector that is measures light such that its signal is substantially insensitive to the absorption by a predetermined gas.

According to another aspect of the present disclosure, the second detector that may have either optical filter attached to it or provided on top of it to make it substantially sensitive to the absorption by the predetermined gas.

According to another aspect of the present disclosure, the opto-electronic package for measurement of absorption of light further comprises many detectors in which at least one detector acts as a reference detector and the other detectors optical filters have applied to them so as to detect different gases present in the cavity.

According to another aspect of the present disclosure, the light source may be a thermal light source.

According to another aspect of the present disclosure, the opto-electronic package for measurement of absorption of light further comprises a substrate with a light source disposed on it. LED may have a center wavelength from 0.2-12 μm.

According to another aspect of the present disclosure, the detector may use direct photon absorption or may use indirect method of measurement that includes conversion to heat to measure light flux.

According to another aspect of the present disclosure, direct photon detectors include detectors made from PbSe, PbS, HgCdTe, GaSb/InAs superlattice etc.

According to another aspect of the present disclosure, indirect thermal detectors include pyroelectrics, bolometers, etc.

According to another aspect of the present disclosure, the opto-electronic package for measurement of absorption of light further comprises that the openings to the cavity that forms the cap may be covered with fine mesh to prevent larger dust particles from entering the cavity.

According to another aspect of the present disclosure, the opto-electronic package for measurement of absorption of light further comprises that the package is constructed with "base package" that can be tested separately from the gas chamber and the two combined by assembly to form the complete gas detection system.

The drawings show exemplary gas detections circuits and configurations. Variations of these circuits, for example, changing the positions of, adding, or removing certain elements from the circuits are not beyond the scope of the present invention. The illustrated smoke detectors, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1:
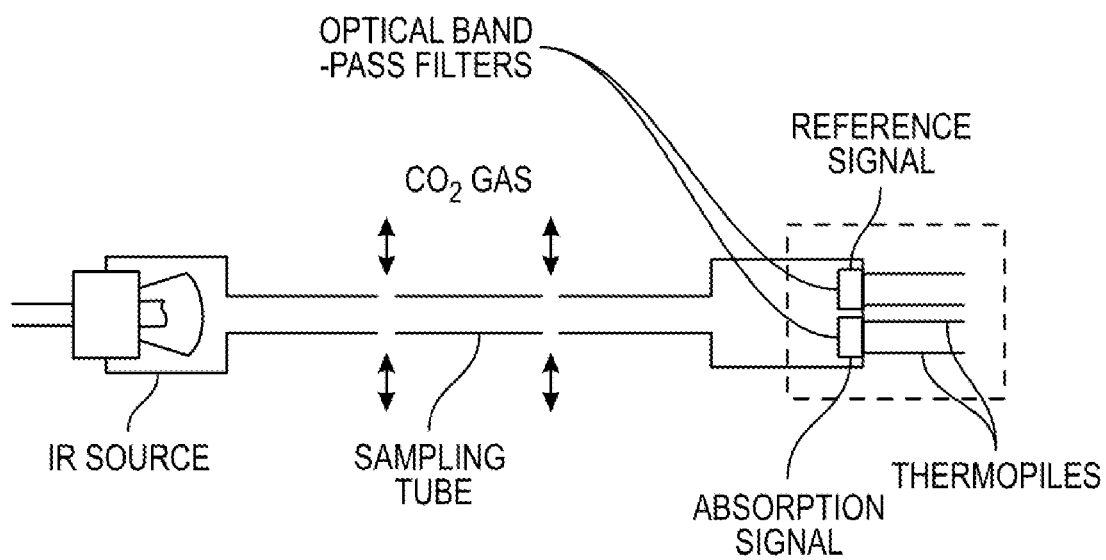
FIG. 1 illustrates an exemplary optical gas detection measurement system utilizing filters disposed proximally to the detectors, in accordance with some embodiments of the disclosure provided herein.

The present disclosure relates to portable gas detection. More specifically, this disclosure describes apparatuses and systems for optical gas detection using differential path. The inventor of the present disclosure contemplates filtering a common beam path, splitting it to measure light absorption at two different light length paths and then calculating the concentration of a predetermined gas.

The following description and drawings set forth certain illustrative implementations of the disclosure in retail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

One of the most popular technique for quantitative measurement of the industrially significant gases such as $CO_2$, $NO_x$, water vapor, methane etc. is carried out by optical absorption. Most of these gases have strong vibrational absorption spectra in the 1-12 μm region of electromagnetic spectrum and include various vibrational modes and its overtones.

A fundamental measurement technique consists of a measuring changes in the extinction of the light source at a particular wavelength of interest as the concentration of the target gas is varied. This technique is popularly called non-dispersive infra-red (NDIR) technique.

Many devices are available on the market. They typically consist of a broadband light source—thermal such as light bulb or a compact heater or an LED—whose output is passed thru an optical system that provides a relatively long path length for absorption of gas and a detector system to measure extinction. Small holes in the optical system allows the gas to diffuse into the light path.

The detector system itself may consist of two detectors. One detector provides a reference signal and is specifically tuned to reduce or avoid gas absorption lines of interest to measure drift and changes in the light source and condition of the optical channel. The other detector is tuned to the wavelength of absorption of the gas to be measured.

Many configurations of the optical systems have been proposed in the past, and some of these devices are available on the market. One of the most popular gases to be measured is $CO_2$. In the discussion below on the design of a novel optical package, the focus will be on $CO_2$ as to make the discussion specific, but the principal applies to many of the industrially relevant gases mentioned earlier and is quite general.

Furthermore, the present disclosure will focus on systems that use room temperature detectors and are not coo ed since cooling adds cost, increases power consumption, and increases system complexity. However, active and/or passive cooling are not beyond the scope of the present invention.

A better method for measuring absolute gas concentration is disclosed. The method applies equally well to absorbance measurement in liquids. This method applies to any fluid (gas or liquid) that can be placed in the path between light source and two detectors.

A large body of literature exists that use reference detector to measure concentration of gas. The argent market is non-dispersive IR measurements (NDIR) in which an optical filter is used to isolate the absorbance of the gas of interest. Some use a single detector and source and pre-calibrated look-up tables to compensate for temperature, humidity, aging etc. while more precise systems use two different detectors with different filter characteristics or vary the filter in time with the same detector. The state of the art looks similar to that in FIG. 1.

FIG. 1 illustrates an exemplary optical gas detection measurement system utilizing filters disposed proximally to the detectors, in accordance with some embodiments of the disclosure provided herein. A light source is powered to shine down a sampling tube. The light source is usually broadband, but the present embodiment uses an infrared (IR) source which is suitable for detecting $CO_2$ gas.

Gas containing $CO_2$ is passed through the sampling tube through vents or ports. Some light absorption occurs as a function of the concentration and chemical composition of the target gas. Meaning, different gasses absorb light at different wavelengths (bandwidths, really). Accordingly, higher concentrations of targeted gasses with absorb more light at that associated wavelength. The goal of any NDIR system is to accurately determine how much light is absorbed/scattered in order to extrapolate the density of gas (i.e., partial pressure of the gas).

The gas in the sample chamber causes absorption of specific wavelengths according to the Beer-Lambert law, and the attenuation of these wavelengths is measured by the detector to determine the gas concentration. Carbon dioxide has a characteristic absorbance band in the infrared (IR) region at a wavelength of 4.26 µm. This means that when IR radiation is passed through a gas containing CO2, part of the radiation is absorbed. Therefore, the amount of radiation passing through the gas depends on the amount of CO2 present, and this can be detected with an IR detector.

As is shown in FIG. 1, this is accomplished by using two optical bandpass filters and two thermopiles. A thermopile is an electronic device that converts thermal energy into electrical energy. It is composed of several thermocouples connected usually in series or, less commonly, in parallel. Such a device works on the principle of the thermoelectric effect, i.e., generating a voltage when its dissimilar metals (thermocouples) are exposed to a temperature difference.

One bandpass filter is used as a reference band and typically doesn't significantly overlap with the absorption signal band. As previously described, the absorption signal band corresponds to the target gas. The two are compared (e.g., ratio, etc.) and a determination can be made about the concentration of the target gas.

A system such as this cues need to be calibrated. Specifically, some measurement baseline needs to be taken before target gas detection. Nevertheless, the present system is susceptible to wavelength drift from the light source, which represents one of the shortcomings of the present state of the art.

Figure 2:
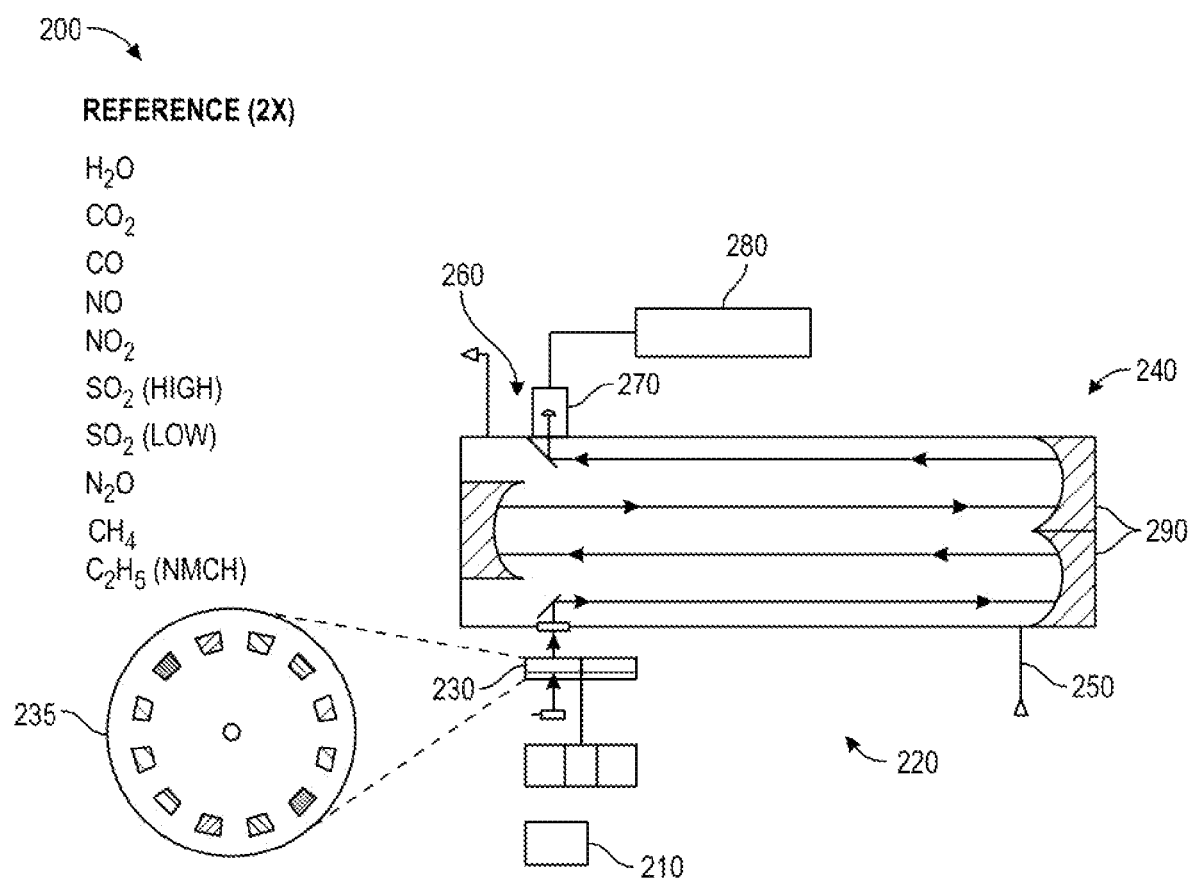
FIG. 2 illustrates an exemplary optical gas detection measurement system utilizing color wheels, in accordance with some embodiments of the disclosure provided herein.

FIG. 2 illustrates an exemplary optical gas detection measurement system 200 utilizing color wheels 235, in accordance with some embodiments of the disclosure provided herein. Optical gas detection measurement system 200 comprises light source 210, optical chopper 230, optical chopper motor 220, sampling volume 240, reflective surfaces 290, inlet 250, outlet 260, detector 270, and electronics 280.

The type of light source 210 is dependent on the gasses detected. In the present embodiment light source 210 is an IR source. While it can, the optical chopper 230 doesn't classically function as a chopper which is known by one of ordinary skill in the art. Meaning, it doesn't modulate a light source into a pulsed (square wave) light signal. Instead, optical chopper spins the color wheel 235 such that it filters the light emanating from light source 210. This is in contrast with the previous embodiment which filters at two different bandwidths at the detectors.

In the present embodiment, color wheel 235 is spun by optical chopper motor 220 and sequences through series of 12 colors. Each color corresponds to target gas, for example, CO, NO, etc. Gas in ingresses though inlet 250 and egressed though outlet 260. One of the objects of the present embodiment is to maximize the pathlength during optical detection thereby augmenting the detected signal at detector 270. This is accomplished by a plurality of reflective surfaces 290 within the sampling volume 240.

In one or more embodiments, the reflective surface is conic section, such as, ellipsoids, paraboloids, or their two-dimensional counterparts. Detector 270 measures the absorption at particular wavelength. Consequently, this get processed by electronic 280, as function of predetermined time dictated by the optical chopper 230 and corresponding color on transmitted through the color wheel 235.

While versatile in that the present embodiment may detect numerous gasses at once, the present system suffers from the previous embodiment. That is, the system requires calibration and is susceptible from wavelength and intensity drift, particularly because it does not have a reference channel measurement.

The idea in the state-of-the-art systems is that the ratio of the reference channel to the filtered channel—corresponding to the specific gas—removes the intensity variation in the source over time as well as common changes in the performance of the detectors. In these methods of measuring gas concentration, shifts in the wavelength spectrum of the light as well as subtle changes in the optical filters cannot be removed directly from the measurement. While alleviating some of the issues of drift, it still requires complex calibration.

Some state-of-the-art systems (e.g., Vaisala) use a Fabry-Perot (FR) cavity-based system use the same detector which receives radiation from a single light source as the filter is tuned alternately between "on gas absorbance" and "off gas absorbance" to measure the gas absorbance. However, this does not properly compensate for the spectral shifts in the light source or the filter. In most of cases of IR measurement of gases, "off-absorption filter" has to be many 100's of nm from the "on-absorption filter" due to the width of the absorption features. This is sufficiently separated in wavelength, that the ratio cannot fully compensate for the spectral shape changes in LED and other light sources over time and temperature.

In all previous designs that the inventor has reviewed, the reference channel uses a different filter than the measurement channel to track the light source's intensity variation. In Vaisala's sensor, FP cavity is used and filter is tuned to be on and off the gas absorption wavelengths alternatively in time.

One of ordinary skill can appreciate the following novel features of the disclosure. Other benefits are not beyond the scope of the present disclosure. The present disclosure is highly independent of the LED and filter performance over temperature, intensity, etc. as well as any changes in the wavelength spectrum of the light source and filters and other optical elements.

Additionally, all spectral changes over are naturally removed from the measurement. This includes changes in intensity either due to electrical or optical system drifts.

The present disclosure provides the benefits of ratio metric measurement cancelling most of the drifts even amongst the two detectors to the extent that the two detectors are identically manufactured.

The present disclosure also provides for highly simplified calibration with a single measurement at a known concentration of the species of interest.

Last, the present disclosure is easy to implement as current solutions are more tractable. As such, calibration procedure is highly simplified during manufacturing.

Figure 3:
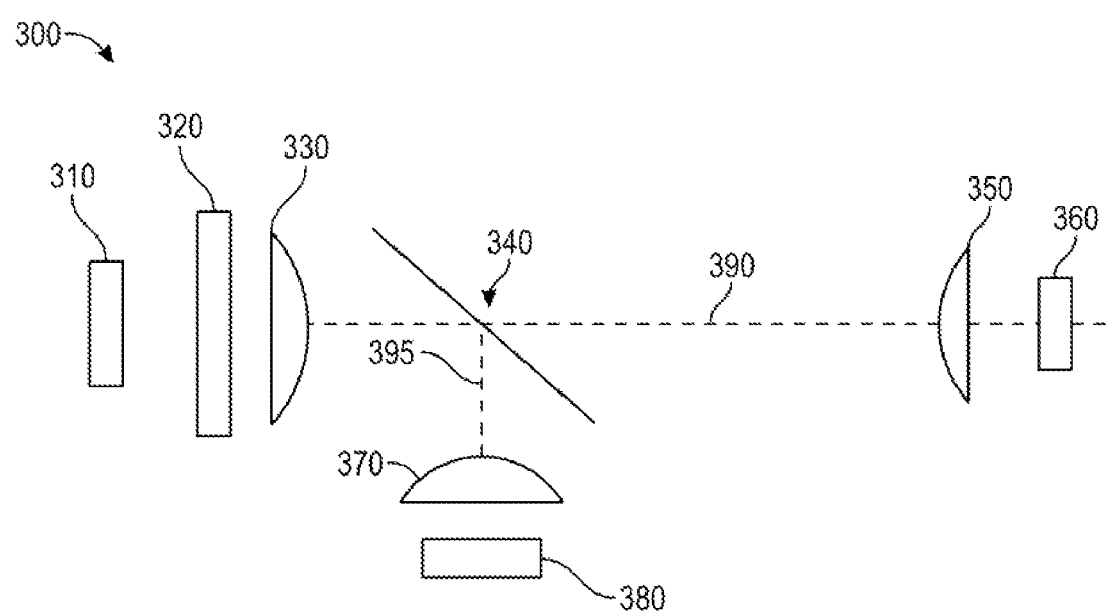
FIG. 3 depicts an exemplary differential path length measurement system for measuring gas concentration using absorption spectroscopy, in accordance with some embodiments of the disclosure provided herein.

FIG. 3 depicts an exemplary differential path length measurement system 300 for measuring gas concentration using absorption spectroscopy, in accordance with some embodiments of the disclosure provided herein. Differential path length measurement system 300 comprises light source 310, filter 320, collimating lens 330, beamsplitter 340, reference collection lens 370, reference detector 380, signal collection lens 350, and signal detector 360.

In one or more embodiments, light source 310 is a light emitting diode (LED), such as, an infrared (IR) light emitting diode. However, other embodiments can have light emitting diodes having shorter wavelengths, such as that in the visible or ultraviolet regime. In yet other embodiments, a plurality of multiple wavelengths can be used. Any suitable, compact light producing device is not beyond the scope of the present disclosure—whether, broadband lamps, coherent, incandescent, incoherent bulb, lasers, or even thermal black-body radiation, etc.

In one or more embodiments filter 320 is a dichroic filter, at least in part. A dichroic filter, thin-film filter, or interference filter is a very accurate color filter used to selectively pass light of a small range of colors while reflecting other colors. By comparison, dichroic mirrors and dichroic reflectors tend to be characterized by the color(s) of light that they reflect, rather than the color(s) they pass.

While dichroic filters are used in the present embodiment, other optical filters are not beyond the scope of the present invention, such as, interference absorption, diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries.

In other embodiments, a color wheel with an optical chopper can be used as the filter 320, pursuant the previous embodiment associated with FIG. 2.

Collimating lens 330 is a collimator. In optics, a collimator may consist of a curved mirror or lens with some type of light source and/or an image at its focus. This can be used to replicate a target focused at infinity with little or no parallax. The purpose of the collimating lens 330 is to direct the light rays in coaxial light path toward beamsplitter 340.

Beamsplitter 340 is a beamsplitter which is known in the art. A beam splitter (or beamsplitter) is an optical device that splits a beam of light in two. It is a crucial part of many optical experimental and measurement systems, such as interferometers, also finding widespread application in fiber optic telecommunications.

In its most common form, a cube, a beamsplitter 340 is made from two triangular glass prisms which are glued together at their base using polyester, epoxy, or urethane-based adhesives. The thickness of the resin layer is adjusted such that (for a certain wavelength) half of the light incident through one "port" (i.e., face of the cube) is reflected and the other ha f is transmitted due to frustrated total internal reflection. Polarizing beam splitters, such as the Wollaston prism, use birefringent materials to split light into two beams of orthogonal polarization states.

In other embodiments, beamsplitter 340 is a half-silvered mirror. This comprises an optical substrate, which is often a sheet of glass or plastic, with a partially transparent thin coating of metal. The thin coating can be aluminum deposited from aluminum vapor using a physical vapor deposition method. The thickness of the deposit is controlled so that part (typically half) of the light which is incident at a 45-degree angle and not absorbed by the coating or substrate material is transmitted, and the remainder is reflected.

A very thin half-silvered mirror used in photography is often called a pellicle mirror, which can also be used in some embodiments. To reduce loss of light due to absorption by the reflective coating, so-called "swiss cheese" beam splitter mirrors have been used. Originally, these were sheets of highly polished meta perforated with ho es to obtain the desired ratio of reflection to transmission. Later, metal was sputtered onto glass so as to form a discontinuous coating, or small areas of a continuous coating were removed by chemical or mechanical action to produce a very literally "half-silvered" surface.

In yet another embodiment, instead of a metallic coating, a dichroic optical coating may be used. Depending on its characteristics, the ratio of reflection to transmission will vary as a function of the wavelength of the incident light. Dichroic mirrors are used in some ellipsoidal reflector spotlights to split off unwanted infrared (heat) radiation, and as output couplers in astir construction.

In still another embodiment, a third version of the beamsplitter 340 is a dichroic mirrored prism assembly which uses dichroic optical coatings to divide an incoming light beam into a number of spectrally distinct output beams. Such a device was used in three-pickup-tube color television cameras and the three-strip Technicolor movie camera. It is currently used in modern three-CCD cameras. An optically similar system is used in reverse as a beam-combiner in three-LCD projectors, in which light from three separate monochrome LCD displays is combined into a single full-color image for projection.

As enumerated, any beam splitter or optical circulator can be used. Optical circulators which have the property to conserve power but greatly increase the complexity and cost. However, any suitable optical device, e.g., polarizing beam splitter, half-wave plate, half silvered mirror, etc., is not beyond the scope of the present invention.

In practice, collimated light coming from collimating lens 330 get bifurcated into two beams, 395, 390. Beam 395 is used as the reference beam, which beam 390 is used as the signal beam. Their geometries are known, as well as their respective pathlengths. The significance of which will be described in greater detail later in the disclosure.

In one or more embodiments, reference collection lens 370 and signal collection lens 350 are optical lenses. An optical lens is a transmissive optical device that focuses or disperses a light beam by means of refraction. A simple lens consists of a single piece of transparent material, while a compound lens consists of several simple lenses (elements), usually arranged along a common axis. Lenses are made from materials such as glass or plastic, and are ground and polished or molded to a desired shape.

A lens can focus light to form an image, unlike a prism, which refracts light without focusing. Devices that similarly focus or disperse waves and radiation other than visible light are also cal ed lenses, such as microwave lenses, electron lenses, acoustic lenses, or explosive lenses.

Most lenses are spherical lenses: their two surfaces are parts of the surfaces of spheres. Each surface can be convex (bulging outwards from the lens), concave (depressed into the lens), or planar (flat). The line joining the centers of the spheres making up the lens surfaces is called the axis of the lens.

Lenses are classified by the curvature of the two optical surfaces. A lens is biconvex (or double convex, or just convex) if both surfaces are convex. If both surfaces have the same radius of curvature, the lens is equiconvex. A lens with two concave surfaces is biconcave (or just concave). If one of the surfaces is flat, the lens is plano-convex or plano-concave depending on the curvature of the other surface. A lens with one convex and one concave side is convex-concave or meniscus. It is this type of lens that is most commonly used in corrective lenses.

If the lens is biconvex or plano-convex, a collimated beam of light passing through the lens converges to a spot (a focus) behind the lens. In this case, the lens is called a positive or converging lens. For a thin lens in air, the distance from the lens to the spot is the focal length of the lens, which is commonly represented by fin diagrams and equations. An extended hemispherical lens is a special type of plano-convex lens, in which the lens's curved surface is a full hemisphere and the lens is much thicker than the radius of curvature.

if the lens is biconcave or plano-concave, a collimated beam of light passing through the lens is diverged (spread); the lens is thus called a negative or diverging lens. The beam, after passing through the lens, appears to emanate from a particular point on the axis in front of the lens. For a thin lens in air, the distance from this point to the lens is the focal length, though it is negative with respect to the focal length of a converging lens.

Convex-concave (meniscus) lenses can be either positive or negative, depending on the relative curvatures of the two surfaces. A negative meniscus lens has a steeper concave surface and is thinner at the center than at the periphery. Conversely, a positive meniscus lens has a steeper convex surface and is thicker at the center than at the periphery. An ideal thin lens with two surfaces of equal curvature would have zero optical power, meaning that it would neither converge nor diverge light.

All real lenses have nonzero thickness, however, which makes a real lens with identical curved surfaces slightly positive. To obtain exactly zero optical power, a meniscus lens must have slightly unequal curvatures to account for the effect of the lens' thickness.

In practice, both collective lenses serve to focus light onto photodetectors 360, 380 are sensors of light or other electromagnetic energy. Photodetector 360, 380 have p-n junctions that converts light photons into current. The absorbed photons make electron-hole pairs in the depletion region, which is used to detect received light intensity. In some embodiments, photodetectors 360, 380 are photodiodes or phototransistors. However, any light detecting means, e.g., avalanche, photo-multiplier tube, etc. is not beyond the scope of the present disclosure.

Pursuant to FIG. 3, it can be demonstrated:

$$R = \frac{S_1}{S_2} = \frac{LSFD_1 \exp(-\alpha_{gas} c_{gas} L_1)}{LSFD_2 \exp(-\alpha_{gas} c_{gas} L_2)} = \frac{D_1}{D_2} \exp(-\alpha_{gas} c_{gas} (L_1 - L_2))$$

Thus, we see that all the variations in the light source and the filter cancel. If the ratio $$\frac{D_1}{D_2}$$

of the responsivities of the detectors is known or calibrated at a known concentration of gas, then one can use this to determine directly any concentration of the gas.

This cancellation of light source characteristics makes the entire detection system independent of the intensity as well as spectral variations in the light source over time, temperature, mechanical stresses and many other parameters that might change the characteristics of LS and filter over time.

Calibration step may be written as:

$$R_0 = \frac{D_1}{D_2} \exp(-\alpha_{gas} c_0 \Delta L)$$

An the ratio noted and saved as part of the instrument calibration.

Now the measurement at any gas concentration may be determined as:

$$\frac{R}{R_0} = \exp(-\alpha_{gas}(c_{gas} - c_0)\Delta L)$$

Or, $$c_{gas} = c_0 + \frac{1}{\alpha_{gas} \Delta L} \log\left(\frac{R}{R_0}\right)$$

Figure 4:
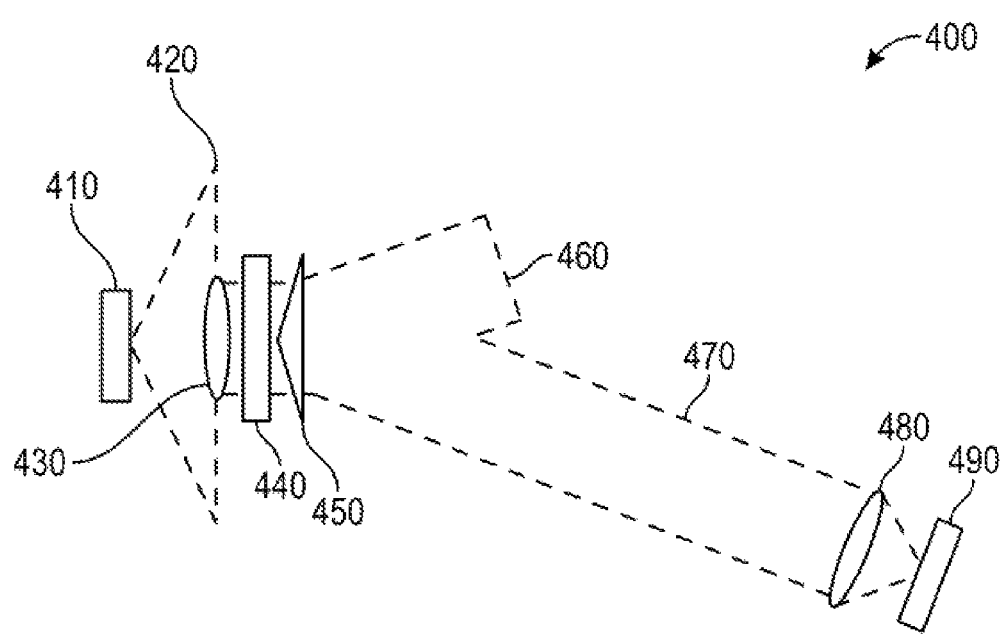
FIG. 4 depicts an exemplary differential path length measurement system for measuring gas concentration using waveguides and alternate optics, in accordance with others embodiments of the disclosure provided herein.

There are many implementations that will achieve the differential path of $\Delta L$. Some of these are drawn in FIG. 4. FIG. 4 depicts an exemplary differential path length measurement system 400 for measuring gas concentration using waveguides and alternate optics, in accordance with others embodiments of the disclosure provided herein.

Differential path length measurement system 400 comprises LED 410, filter 440, collimating lens 430, Fresnel prism 450, reference detector (not shown), signal collection lens 480, and signal detector 490. In practice, light 420 is emitted from LED 410 in a conical shape—usually 15 to 20 degrees in divergence. Collimating lens 430 collimates the light to substantially parallel light ray axes, however, this is not entirely necessary.

In one or more embodiments, Fresnel prism 450 is a is a Frenal lens used to split the beam into two pathways. A Fresnel lens is a type of composite compact lens originally developed by French physicist Augustin-Jean Fresnel (1788-1827) for lighthouses. It has been called "the invention that saved a million ships."

The design allows the construction of lenses of large aperture and short focal length without the mass and volume of material that would be required by a lens of conventional design. A Fresnel lens can be made much thinner than a comparable conventional lens, in some cases taking the form of a flat sheet. A Fresnel lens can capture more oblique light from a light source, thus allowing the light from a lighthouse equipped with one to be visible over greater distances.

After separation, reference light 460 to a reference detector (not shown), while signal light 470 interacts with ambient gas and travels to collection lens 480. Collection lens 480 focusses the light to signal detector 490 for comparison to reference detector.

One may argue that the ratio $$\frac{D_1}{D_2}$$

of the responsivities of the detectors will change over time. This is clearly not included in the calculations above. It is easy to see that these variations will be much smaller than the conventional technique. This is partly from the fact that the responsivities of the two detectors—even if identically constructed are likely to drift apart over time if the wavelength spectrum is drastically different and they receive very different amount of light flux. In our case, the two detectors are assumed identically manufactured and for all practical purposes receive the same spectrum of light. If each of the detectors drifted with some parameter such as temperature, we can write the ratio as:

$$\frac{D_1}{D_2} = \frac{D_{10}(1+\alpha_1 T)}{D_{20}(1+\alpha_2 T)}$$

The changes in responsivity (say over temperature here but it could be any other parameter will be quite similar and hence we may write $\alpha_2 = \alpha_1 + \delta\alpha$, and simplify the above equation:

$$\frac{D_1}{D_2} \sim \frac{D_{10}(1+\alpha_1 T)}{D_{20}}$$

So, for a typical mid wave IR detector, $\alpha$ itself may be varying at part per thousand per kelvin out relative tracking between the two detectors is easily another two or three orders of magnitude better. Thus, the error in the ratio of the responsivities is reduced by another two orders of magnitude. Thus, even over 50-100 K temperature range, one can maintain the ratio to better than 1% and perhaps as good as 0.01% depending on the detector technology.

Figure 5:
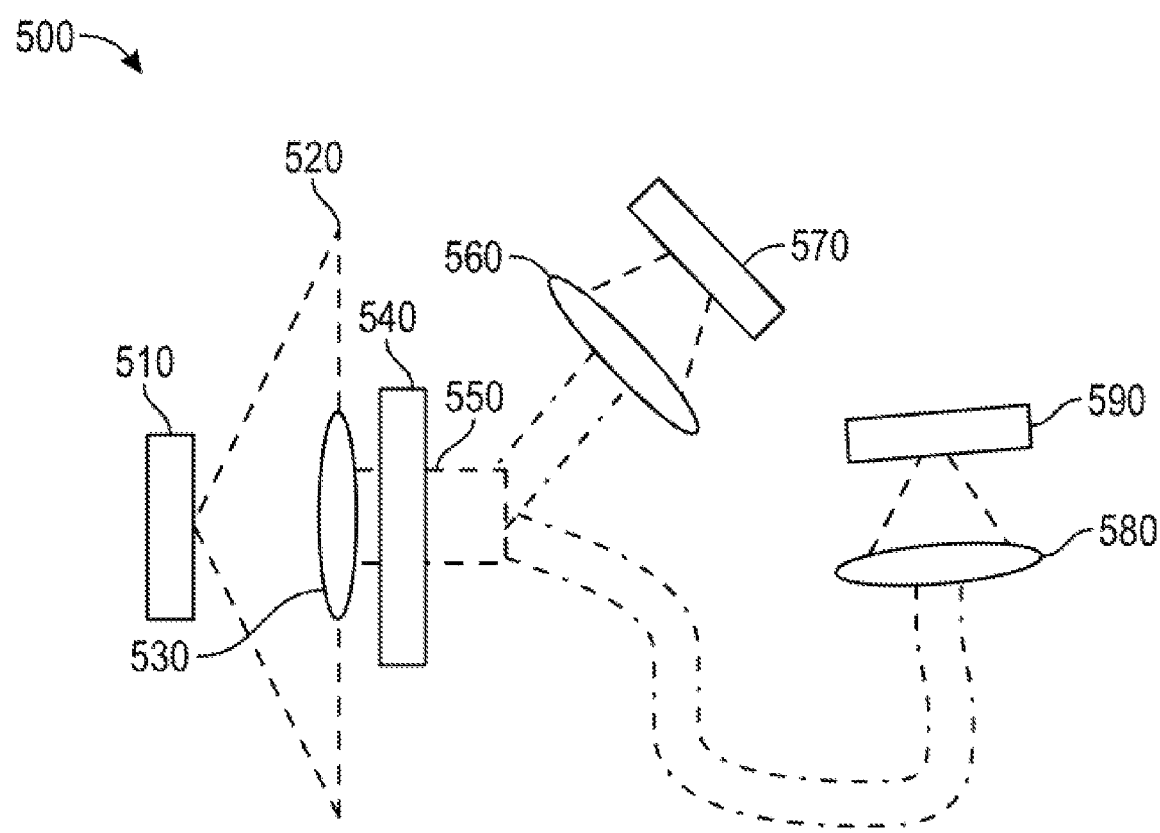
FIG. 5 depicts an exemplary differential path length measurement system for measuring gas concentration using waveguides and alternate optics, in accordance with others embodiments of the disclosure provided herein.

FIG. 5 depicts an exemplary differential path length measurement system 500 for measuring gas concentration using waveguides and alternate optics, in accordance with others embodiments of the disclosure provided herein. Differential path length measurement system 500 comprises LED 510, filter 540, collimating lens 530, waveguide 550, reference detector 570, reference collection lens 560, signal collection lens 580, and signal detector 590. In practice, light 520 is emitted from LED 510 in a conical shape—usually 15 to 20 degrees in divergence. Collimating lens 530 collimates the light to substantially parallel light ray axes, however, this is not entirely necessary.

In one or more embodiments, waveguide 550 is a hollow waveguide which is couplet to two more waveguides which serve to beam split the incoming light. A waveguide is a structure that guides waves, such as electromagnetic waves or sound, with minimal loss of energy by restricting the transmission of energy to one direction. Without the physical constraint of a waveguide, wave amplitudes decrease according to the inverse square law as they expand into three-dimensional space.

There are different types of waveguides for different types of waves. The original and most common meaning is a hollow conductive metal pipe used to carry high frequency radio waves, particularly microwaves. Dielectric waveguides are used at higher radio frequencies, and transparent dielectric waveguides and optical fibers serve as waveguides for light. In acoustics, air ducts and horns are used as waveguides for sound in musical instruments and loudspeakers, and specially-shaped metal rods conduct ultrasonic waves in ultrasonic machining.

The geometry of a waveguide reflects its function; in addition to more common types that channel the wave in one dimension, there are two-dimensional slab waveguides which confine waves to two dimensions. The frequency of the transmitted wave also dictates the size of a waveguide: each waveguide has a cutoff wavelength determines by its size and will not conduct waves of greater wavelength; an optical fiber that guides light will not transmit microwaves which have a much larger wavelength. Some naturally occurring structures can also act as waveguides.

Figure 6:
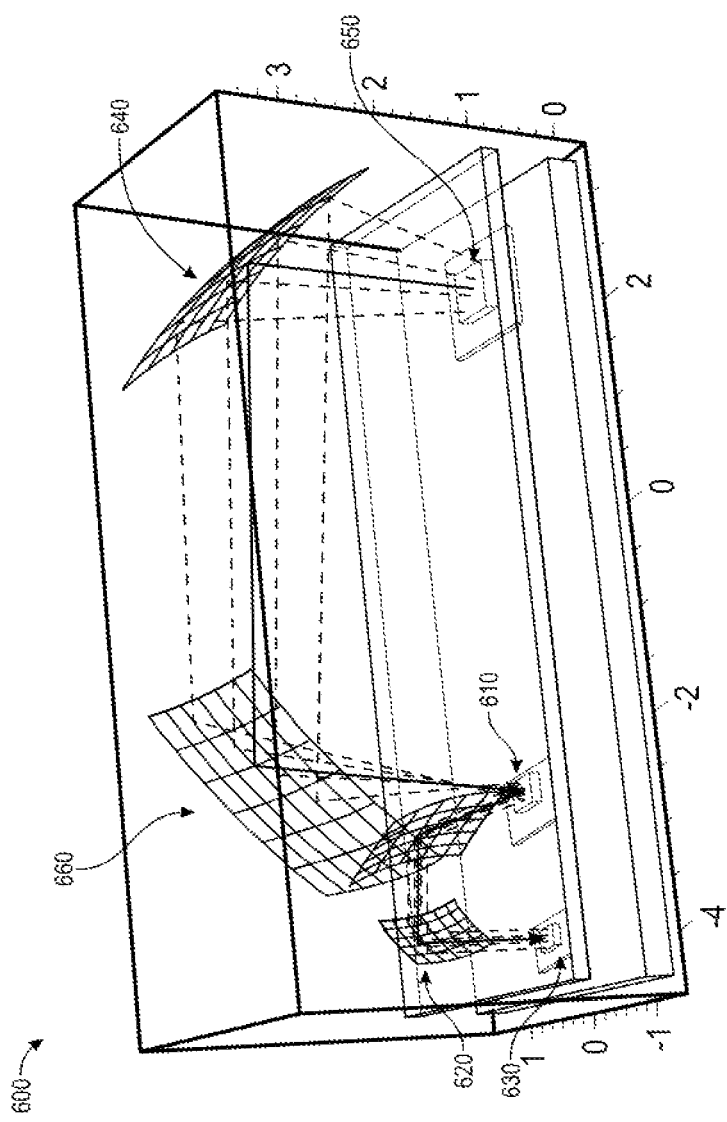
FIG. 6 illustrates an exemplary 3-dimensional perspective of a differential path length measurement system for measuring gas concentration using an optical conic-section cap, in accordance with others embodiments of the disclosure provided herein.

FIG. 6 illustrates an exemplary 3-dimensional perspective of a differential path length measurement system 600 for measuring gas concentration using an optical conic-section cap, in accordance with others embodiments of the disclosure provided herein. Differential path length measurement system 600 comprises light source 610, reflector 620, reference detector 630, primary signal reflector 660, secondary reflector 640, and signal detector 650.

In the present embodiment, the differential path length measurement apparatus 600 uses two different reflective surfaces disposed close to one another, rather than some beam splitting optic, e.g., PBS, half-wave plate, half-silvered, etc.

In this or other embodiments, the reference and signal paths are split using a three-dimensional optical cap which can be packaged onto the printer circuit board (PCB) and chip assembly. In the context of the optical reference pathway, a plurality of photons impinges on an ellipsoid. These consequently get reflected and redirected to one (or more) or its foci, at which a photodetector is disposed.

The alternate pathway in accordance with FIG. 6 s the optical signal pathway. While similarly measured, the pathway is longer. The optical path length between the signal and the reference pathway is called the effective path length and used for absorption calculations which have previously been described. In one or more embodiments, the optical signal pathway, a plurality of photons emanating from a light source (e.g., LED, etc.) impinge upon a paraboloid. These consequently get reflected and redirected to its foci, at which a photodetector is disposed.

While an ellipsoid is used for the reference measurement and paraboloid is utilized for the signal channel pathway, any suitable conic-section is not beyond the scope of the present disclosure. Even still, with the use of waveguides or other optics, 2-dimensional substitutes may be used, such that, parabolas and ellipses.

Figure 7:
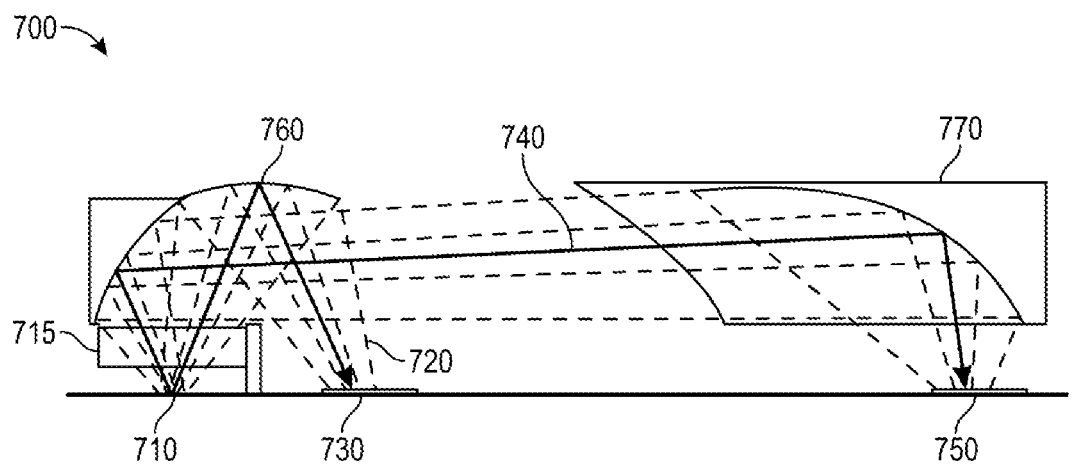
FIG. 7 illustrates an exemplary 2-dimensional ray-trace of a differential path length measurement system for measuring gas concentration using an optical conic-section cap, in accordance with others embodiments of the disclosure provided herein.

FIG. 7 illustrates an exemplary 2-dimensional ray-trace of a differential path length measurement system 700 for measuring gas concentration using an optical conic-section cap, in accordance with others embodiments of the disclosure provided herein. Differential path length measurement system 700 comprises light source 710, reflector 760, reference detector 730, filter 715, signal reflector 770, and signal detector 750.

In the present embodiment, the differential path length measurement apparatus 700 uses two different reflective surfaces disposed close to one another, rather than some beam splitting optic, e.g., PBS, half-wave plate, half-silvered, etc. In practice, light is emitted from light source 710 and projected trough filter 715. It is then subsequently is reflected off of reflector 760 while reference light 720 progresses to reference detector 730.

Signal light 740, which inherently has a longer pathlength becomes incident on signal reflector 770. In turn, signal light 740 is measured at signal detector 750 where it is compared to reference detector 730.

In more or more embodiments, reflector 760 and signal reflector 770 are conic sections. In mathematics, a conic section (or simply conic) is a curve obtained as the intersection of the surface of a cone with a plane. The three types of conic section are the hyperbola, the parabola, and the ellipse; the circle is a special case of the ellipse, though historically it was sometimes called a fourth type.

The conic sections in the Euclidean plane have various distinguishing properties, many of which can be used as alternative definitions. One such property defines a noncircular conic to be the set of those points whose distances to some particular point, called a focus, and some particular line, called a directrix, are in a fixed ratio, called the eccentricity. The type of conic is determined by the value of the eccentricity. In analytic geometry, a conic may be defined as a plane algebraic curve of degree 2; that is, as the set of points whose coordinates satisfy a quadratic equation in two variables. This equation may be written in matrix form, and some geometric properties can be studied as algebraic conditions.

In the Euclidean plane, the three types of conic sections appear quite different, but share many properties. By extending the Euclidean plane to include a line at infinity, obtaining a projective plane, the apparent difference vanishes: the branches of a hyperbola meet in two points at infinity, making it a single closed curve; and the two ends of a parabola meet to make it a closed curve tangent to the line at infinity. Further extension, by expanding the real coordinates to admit complex coordinates, provides the means to see this unification algebraically.

Here, in the present embodiment, the reference channel pathway shares the same conic-section reflection surface reflection. However, cue to its known pathway towards the reference detection, a calculation of gas absorption can be made. It is noted that the second signal path also reflects upon the conic-section cap but impinges upon the signal detector (main).

In one or more embodiments, a filter is disposed proximally to the light source. These are chosen for the gas detection purposes. Specifically, to increase signal-noise-ratio (SNR), optical bandpass filters are implemented to optimize the photon-gas absorption. In other embodiments, these can be a combination of optical components, e.g., a combination of low and high pass filters disposed near the light source.

While dichroic filters are used in the present embodiment, other optical filters are not beyond the scope of the present invention, such as, interference, absorption, diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries.

Figure 8:
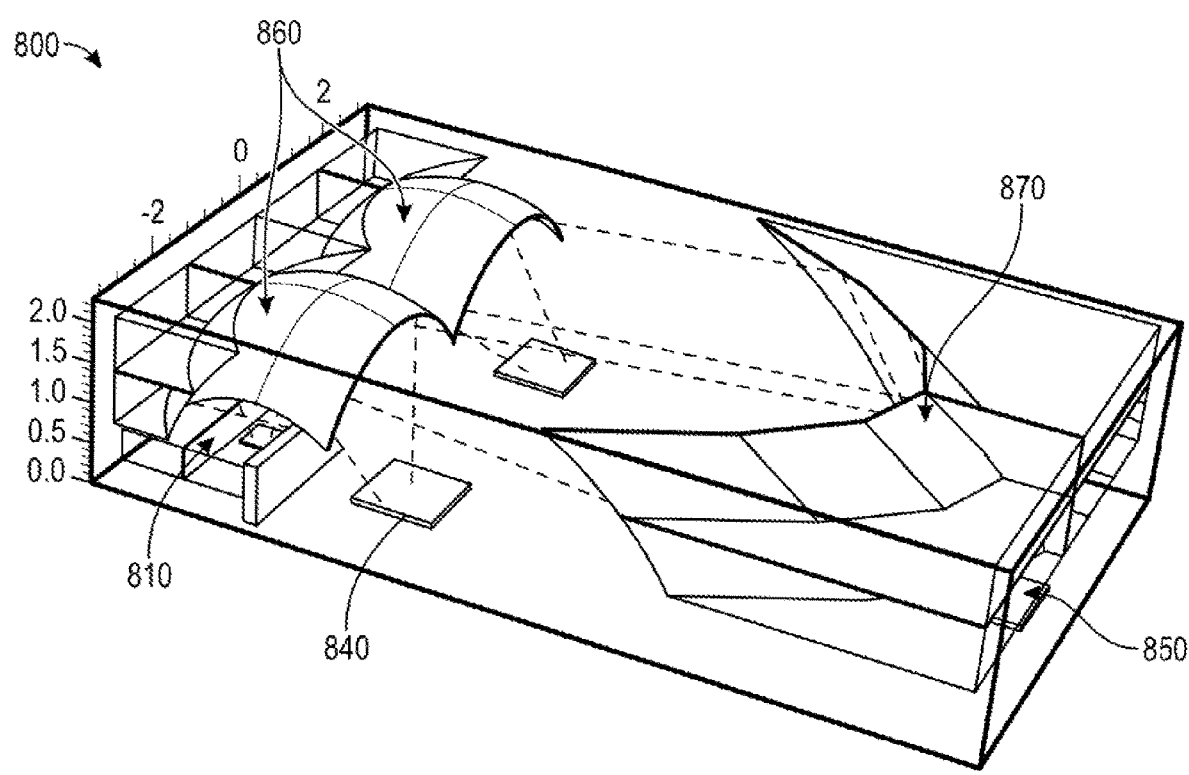
FIG. 8 is an isometric view of an exemplary 3-dimensional perspective of a differential path length measurement system for measuring 2 gas concentrations using an optical conic-section cap, in accordance with others embodiments of the disclosure provided herein; and, FIG. 9 illustrates an exemplary 2-dimensional ray-trace of a differential path length measurement system for measuring 2 gas concentrations using an optical conic-section cap, in accordance with others embodiments of the disclosure provided herein.

FIG. 8 is an isometric view of an exemplary 3-dimensional perspective of a differential path length measurement system 800 for measuring 2 gas concentrations using an optical conic-section cap, in accordance with others embodiments of the disclosure provided herein.

Differential path length measurement system 800 comprises light source 810, reflectors 860, reference detectors 840, signal reflector 870, and signal detector 850. In the present embodiment, two light sources with two different color filters are implemented.

FIG. 8 illustrates an exemplary 3-dimensional perspective of a differential path length measurement system for measuring 2 gas concentrations using an optical conic-section cap, in accordance with others embodiments of the disclosure provided herein. In the present embodiment, a plurality of source and corresponding filters get reflected off a multi-dimensional configuration similar to that depicted in FIG. 7.

However, in the present embodiment, this can be used to detect multiple gases using a sing e detector, provided suitable filtering at the light sources. This retains the strategy of using reference channel and main longer path channel which works for more than one gas. As depicted, there are two reference detector sand one main photo-detector.

The reflective surface of the conic section cap can be made in a variety of ways, all of which are not beyond the scope of the present invention. All conductive/reflective materials remain within the scope of the present disclosure. By way of example, either or both the surfaces exhibit a highly mirrored surface.

This coating can be performed by, for example but not limited to: direct metal deposition (DMD); laser metal deposition (LMD), thin-film deposition; chemical solution deposition (CSD), chemical bath deposition (CBD), chemical vapor deposition (CVD), plasma enhanced CVD (PECVD), atomic layer deposition (ALD), molecular layer deposition (MLD), physical vapor deposition (PVD), electroplating and sputtering.

The reflective materials comprised by the cap surface Include, but not limited to: metal, metal alloys, compound metals, semi-conductors, conductive and semi-conductive polymers, conductive and semi-conductive composites, graphene, carbon nanotube, and graphite.

In one or more embodiments, an LED is used instead of laser to measure the fiber brag grating (FBG) as a sensor. Collimating optics are used to control Etendue which is a property of light in an optical system, which characterizes how spread out the light is in area and angle.

From the source point of view, it is the product of the area of the source and the solid angle that the system's entrance pupil subtends as seen from the source. Equivalently, from the system point of view, the etendue equals the area of the entrance pupil times the solid angle the source subtends as seen from the pupil. These definitions must be applied for infinitesimally small elements of area and solid angle, which must then be summed over both the source and the diaphragm as shown below. Etendue may be considered to be a volume in phase space.

Etendue is important because it never decreases in any optical system where optical power is conserved. A perfect optical system produces an image with the same etendue as the source. The etendue is related to the Lagrange invariant and the optical invariant, which share the property of being constant in an ideal optical system. The radiance of an optical system is equal to the derivative of the radiant flux with respect to the etendue.

In some embodiments, detector cover, optical chamber, waveguides and other elements are covered in high conductivity (mirrored) or any other suitable material, e.g., metal, semi-metallic, composite, which are a so not beyond the scope of the present disclosure. In embodiments, elements can be made of a polymer or silicon and silvered using deposition techniques known in the art.

In some embodiments, photosensitive elements are sensors of light or other electromagnetic energy. In a preferred embodiment, the photosensitive elements are photodetector which have p-n junctions that converts light photons into current. The absorbed photons make electron-hole pairs in the depletion region, which is used to detect received light intensity. In some other embodiments, photodetector are photodiodes or phototransistors. However, any light detecting means, e.g., avalanche photodiodes (APDs), single-photon avalanche photodiode (SPADs), and photomultipliers tubes (PMTs) are not beyond the scope of the present disclosure.

In one or more embodiments, a dichroic filter, thin-film filter, or interference filter is used as a very accurate color filter used to selectively pass light of a small range of colors while reflecting other colors. By comparison, dichroic mirrors and dichroic reflectors tend to be characterized by the color(s) of light that they reflect, rather than the color(s) they pass.

While dichroic filters are used in the present embodiment, other optical filters are not beyond the scope of the present invention, such as, interference, absorption, Diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries.

Figure 9:
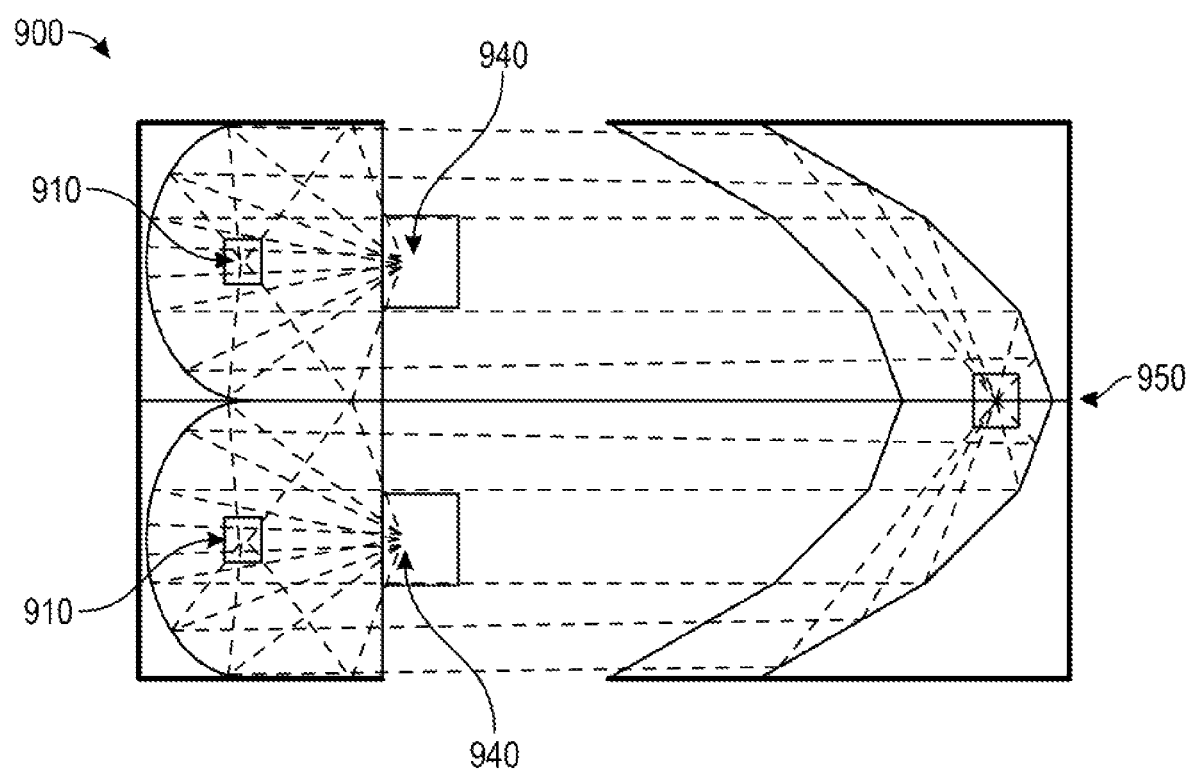

FIG. 9 illustrates an exemplary 2-dimensional ray-trace of a differential path length measurement system 900 for measuring 2 gas concentrations using an optical conic-section cap, in accordance with others embodiments of the disclosure provided herein.

Differential path length measurement system 900 comprises light sources 910, reference detectors 940, signal reflector 970, and signal detector 950. In the present embodiment, two light sources with two different color filters are implemented.

In one or more embodiments, light sources 910 are different colors which are optimized for different detectable gasses. Specifically, the bandwidth centered at particular frequency is chosen to reflect that of the resonant frequency of a predetermined chemical. That is, the frequency (or wavelength) of light which get absorbed by the chemical of interest.

This enables the detection of two gasses, each of which having their own reference pathway. In the present embodiment. In the present embodiment, this can be implement using the same signal detector by alternating the color on and off. An ASIC or analog front end (AFE) can them separate the signal and make the appropriate calculation which will be discussed in further detail later in the disclosure.

An application-specific integrated circuit (ASIC) is an integrated circuit (IC) chip customized for a particular use, rather than intended for general-purpose use. For example, a chip designed to run in a digital voice recorder or a high-efficiency bitcoin miner is an ASIC.

An analog front-end (AFE or analog front-end controller AFEC) is a set of analog signal conditioning circuitry that uses sensitive analog amplifiers, often operational amplifiers, filters, and sometimes application-specific integrated circuits for sensors, radio receivers, and other circuits to provide a configurable and flexible electronics functional block, needed to interface a variety of sensors to an, antenna, analog to digital converter or in some cases to a microcontroller.

In an alternate embodiment, a sing e gas is detected, whereas the second pathway is used so e to detect and correct for environmental changes, temperature, gain, current, etc. Again, this obviates the need for factory calibration.

As has been demonstrated, there is cancellation of intensity and wavelength shift of the LED over temperature and other environmental parameters. Note that common-mode shifts in temperature performance of the photodetector and the amplifier denoted by D is a so compensated.

This is shown in the equation below:

$$R_1 = \frac{S_{1Main}}{S_{1Ref}} =$$

$$\frac{L_1 F_1 \eta_{Main} D_{1Main} \exp(-\alpha_{gas} c_{gas} L_1)}{L_1 F_1 \eta_{Ref} D_{1Ref} \exp(-\alpha_{gas} c_{gas} L_2)} = \frac{\eta_{Main} D_{1Main}}{\eta_{Ref} D_{1Ref}} \exp(-\alpha_{gas} c_{gas}(L_1 - L_2))$$

Note that η represents optical splitting efficiency of the LED light as portion of the light is sent to the main detector and another portion sent to the reference detector. As one can see from the equation, the optical splitting is not cancel ed and any changes in the ratio $\eta_{Main}/\eta_{Ref}$ can't be distinguished from the exponential term representing absorption by the gas.

For example, if the beam splitter (reflectors 860) shifts relative to the LED/PDs cue to any reason (e.g. from stress or expansion/contraction due to temperature), it may increase the light going to signal detector 950 and decrease it to reference detectors 940 thus changing the ratio $\eta_{Main}/\eta_{Ref}$. Another object of this alternate embodiment is to compensate for it also.

If the first and second light pathways are substantially similar in length and optics but the second absorbs no light, two measurement can be made. First using the first LED that measures the gas absorption and then immediately measure using the second LED that is known to be not absorbed by any other gas that might be present. Ratio at the second LED wavelength will look just like the previous equation except for the missing absorption term. This is written as:

$$R_2 = \frac{S_{2Main}}{S_{2Ref}} = \frac{L_2 F_2 D_{2Main}}{L_2 F_{21} \eta_{Ref} D_{2Ref}} = \frac{\eta_{Main} D_{2Main}}{\eta_{Ref} D_{2Ref}}$$

Now we can form the ratio of ratio (RoR) and it can be readily seen that Θ's will cancel too. Thus, RoR will eliminate any drift caused by mechanical shift of the optical components either from stress or temperature. RoR is:

$$RoR = \frac{R_1}{R_2} =$$

$$\frac{\frac{\eta_{Main} D_{1Main}}{\eta_{Ref} D_{1Ref}} \exp(-\alpha_{gas} c_{gas}(L_1 - L_2))}{\frac{\eta_{Main} D_{2Main}}{\eta_{Ref} D_{2Ref}}} = \frac{\left(\frac{D_{1Main}}{D_{2Main}}\right)}{\left(\frac{D_{1ref}}{D_{2Ref}}\right)} \exp(-\alpha_{gas} c_{gas}(L_1 - L_2))$$

Consider the first term:

$$\left(\frac{D_{1Main}}{D_{2Main}}\right).$$

This ratio is measured on a physically the same detector connected to the same electronics. Any changes in the detector characteristics that are common to both the wavelengths such as amplifier gain, detector's shunt impedances, etc. and will all cancel as a function of temperature or some other environmental parameter. A potentially small and residual wavelength dependent change in these parameters may remain uncompensated. But the second term $$\left(\frac{D_{1ref}}{D_{2Ref}}\right)$$

has the same characteristics—as it is made from the same material and made together in manufacturing process and will divide the first term in the previous equation and thus the pre-factor as demonstrated below:

$$\gamma \equiv \frac{\left(\frac{D_{1Main}}{D_{2Main}}\right)}{\left(\frac{D_{1ref}}{D_{2Ref}}\right)}$$

where, $\gamma$ is the maximum extent possible independent of the environmental factors. Consequently, calibration is performed as follows.

In the absence of any gas, the previous equation can be written as:

$RoR(c_{gas}=0)=\gamma$

This ratio can be saved in memory and then the gas concentration is measured by:

$$\frac{RoR(c_{gas})}{RoR(c_{gas}=0)} = \exp(-\alpha_{gas}c_{gas}(L_1 - L_2)) \approx 1 - \alpha_{gas}c_{gas}(\Delta L)$$

The approximate right-hand term of the previous equation applies when the argument of exponential is small.

With this method, the inventor of the present disclosure has achieved direct calibration free measurement of gas concentration. It only requires the knowledge of optical path length and average gas absorption $\alpha_{gas}$. Note that for many popular gases such as $CO_2$ or $CH_4$ etc. absorption cross-section can be calculated for a given LED and optical filter.

In general, $2^{nd}$ LED and the $1^{st}$ LED after passing through the filter can both have common absorption regions. In which case, the common absorption region will still be cancelled.

In one or more embodiments employing multiple photodetectors, thin film interference coating could be used to collect light at a predetermined incident angle. That is, detectors closer to the septum could have filters which would collect more normal (orthogonal) light. Whereas, detectors further away could be optimized to collect light of lower incident angles, such as, 45-60 degrees. That way, in practice, more weighting could be given to light that has been scattered close by.

While the present disclosure primarily focuses on gaseous chemical detection, other devices are not beyond the scope of the invention. For example, fire safety systems are entirely applicable.

SELECT EXAMPLES

Example 1 provides an optical differential path length gas detector comprising a light source producing a first light, a light filter disposed proximally to the light source, a beam-spitting optic configured to split the light into two pathways, a second and third light, respectively, after having passed through the light filter, a first photodetector configured to measure the second light, wherein the first photodetector is configured to have a shorter pathlength than the third light, and a second photodetector configured to measure the third light, wherein the second photodetector is configured to have a longer pathlength relative to the second.

Example 2 provides an optical differential path length gas detector of example 1 further comprising a lens disposed in the first light path between the light source and the light filter.

Example 3 provides an optical differential path length gas detector of example 1, wherein the light filter is centered at a first predetermined wavelength.

Example 4 provides an optical differential path length gas detector of example 1 optical differential path length gas detector of example 1, wherein the light filter comprises a plurality of colors.

Example 5 provides an optical differential path length gas detector of example 1 optical differential path length gas detector of example 1, wherein the light filter is a color wheel driven by an optical chopper.

Example 6 provides an optical differential path length gas detector of example 1 optical differential path length gas detector of example 1, wherein the beamsplitter optic is a polarizing beam splitter.

Example 7 provides an optical differential path length gas detector of example 1 optical differential path length gas detector of example 1, wherein the beamsplitter optic is a half-silvered mirror.

Example 8 provides an optical differential path length gas detector of example 1 optical differential path length gas detector of example 1, wherein the beamsplitter optic is a Fresnel prism.

Example 9 provides an optical differential path length gas detector of example 1 optical differential path length gas detector of example 1, wherein the beamsplitter optic is a waveguide.

Example 10 provides an optical differential path length gas detector of example 1 optical differential path length gas detector of example 1, further comprising a lens disposed in the second pathway between the beamsplitter optic and first photodetector.

Example 11 provides an optical differential path length gas detector of example 1 further comprising a lens disposed in the third pathway between the beamsplitter optic and second photodetector.

Example 12 provides an optical differential path length gas detector of example 1 further comprising waveguides disposed between beam-spitting optic and first and second photodetector.

Example 12 provides an optical differential path length gas detector of example 1 further comprising a circuit configure to calculated a ratio of measurements between the first and second photodetectors.

Example 14 provides an optical differential path length gas detector comprising a light source producing a first light, a light filter disposed proximally to the light source, a first conic-section optic configured to split the light into two pathways, a second and third light, respectively, after having passed through the light filter, a first photodetector configured to measure the second light, wherein the first photodetector is configured to have a shorter pathlength than the third light; and a second conic-section optic configured to direct the third light to a second photodetector; wherein the second photodetector is configured to measure the third light.

Example 15 provides an optical differential path length gas detector of example 14 wherein the light filter is centered at a first predetermined wavelength.

Example 16 provides an optical differential path length gas detector of example 15, wherein the light filter comprises a plurality of colors.

Example 17 provides an optical differential path length gas detector of example 16 wherein the light filter is a color wheel driven by an optical chopper.

Example 18 provides an optical differential path length gas detector of example 14 further comprising a circuit configure to calculated a ratio of measurements between the first and second photodetectors.

Example 19 provides an optical differential path length gas detector comprising a first light source producing a first light, a first light filter disposed proximally to the first light source, a first conic-section optic configured to direct the first light towards a third conic-section optic, a second light source producing a second light, a second light filter disposed proximally to the second light source, a second conic-section optic configured to direct the second light towards the third conic-section optic, a photodetector configured to measure the first and second light, wherein, the third conic-section optic is configured to direct the first and second light toward the photodetector.

Example 20 provides an optical differential path length gas detector comprising example 19 further comprising a time multiplexer, wherein the time multiplexer is configured alternate between measurement of the first and second light.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skillet in the art will recognize, or one able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is induced within the scope of the present disclosure.

The foregoing outlines features of one or more embodiments of the subject matter disclosed herein. These embodiments are provided to enable a person having ordinary skip in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that the may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particular those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at east some portions of the processing activities outlined herein may also be implemented in software. In some embodiments, one or more of these features may be implemented in hardware provided external to the elements of the disclosed figures, or consolidates in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that induces digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (FDA), a smart phone, a mobile phone, an iPad, or any other suitable portable or fixed electronic device.

Also, a computer may have one or more input and output devices. These devices can be uses, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (N) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure.

Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converter (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the boars based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provides herein, interaction may be described in terms of two, three, four, or more electrical components. However, this has been cone for purposes of clarity and example only. It should be appreciated that the system can be consolidated in any suitable manner. Along similar design alternatives, any of the illustrates components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicates/sophisticated arrangements and configurations. Accordingly, the examples provided should not limit the scope or inhibit the broad teachings of the electrics circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above" "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at east one of A and/or B") may refer, in one embodiment, to at least one, optionally including more than one, A, with no B present (and optionally including elements other than B); in another embodiment, to at least one, optionally including more than one, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An optical differential path length gas detector comprising:
    a light source producing a first light;
    a light filter disposed proximally to the light source;
    a first conic-section optic configured to split the light into two pathways, a second and third light, respectively, after having passed through the light filter;
    a first photodetector configured to measure the second light, wherein the first photodetector is configured to have a shorter pathlength than the third light; and
    a second conic-section optic configured to direct the third light to a second photodetector;
    wherein the second photodetector is configured to measure the third light.

2. The optical differential path length gas detector of claim 1, wherein the light filter is centered at a first predetermined wavelength.

3. The optical differential path length gas detector of claim 1, wherein the light filter comprises a plurality of colors.

4. The optical differential path length gas detector of claim 3 wherein the light filter is a color wheel driven by an optical chopper.

5. The optical differential path length gas detector of claim 1 further comprising a circuit to calculate a ratio of measurements between the first and second photodetectors.

6. The optical differential path length gas detector of claim 1, wherein the first conic-section optic is a conic section reflector.

7. The optical differential path length gas detector of claim 6, wherein the conic section reflector is a parabola at least in two dimensions.

8. The optical differential path length gas detector of claim 6, wherein the conic section reflector is an ellipse at least in two dimensions.

9. The optical differential path length gas detector of claim 6, wherein the conic section reflection is a hyperbola at least in two dimensions.

10. The optical differential path length gas detector of claim 1, wherein the first light has a first pathway, and further comprising a lens disposed in the first light pathway between the light source and the light filter.

11. The optical differential path length gas detector of claim 1, further comprising a lens disposed between the light filter and the first photodetector.

12. An optical differential path length gas detector comprising:
    a first light source producing a first light;
    a first light filter disposed proximally to the first light source;
    a first conic-section optic configured to direct the first light towards a third conic-section optic;
    a second light source producing a second light;
    a second light filter disposed proximally to the second light source;
    a second conic-section optic configured to direct the second light towards the third conic-section optic; and
    a photodetector configured to measure the first and second light;
    wherein, the third conic-section optic is configured to direct the first and second light toward the photodetector.

13. The optical differential path length gas detector of claim 12 further comprising a time multiplexer, wherein the time multiplexer is configured alternate between measurement of the first and second light.

14. The optical differential path length gas detector of claim 12, wherein the first conic-section optic is a conic section reflector.

15. The optical differential path length gas detector of claim 14, wherein the conic section reflector is a parabola at least in two dimensions.

16. The optical differential path length gas detector of claim 14, wherein the conic section reflector is an ellipse at least in two dimensions.

17. The optical differential path length gas detector of claim 14, wherein the conic section reflection is a hyperbola at least in two dimensions.

18. A method for optical differential path length gas detector comprising:
    producing a first light at a first light source;
    filtering the first light at a light filter disposed proximally to the light source;
    splitting, at a first conic-section optic, the filtered first light into two pathways, a second and third light, respectively;
    measuring the second light at a first photodetector, wherein the first photodetector is configured to have a shorter pathlength than the third light;
    directing, at a second conic-section optic, the third light to a second photodetector; and
    measuring the third light at the second photodetector.

19. The method of claim 18, further comprising calculating a ratio of measurements between the first and second photodetectors.

20. The method of claim 18, further comprising alternating, at a time multiplexor, between measuring the second light and the third light.

* * * * *